(12) United States Patent
Herlitz

(10) Patent No.: US 8,914,485 B2
(45) Date of Patent: Dec. 16, 2014

(54) METHODS AND APPARATUS FOR IN-PROCESS CLIENT-SIDE CONTEXT MANAGERS

(75) Inventor: Sten Herlitz, Boston, MA (US)

(73) Assignee: General Electric Company, Schenectady, NY (US)

(*) Notice: Subject to any disclaimer, the term of this patent is extended or adjusted under 35 U.S.C. 154(b) by 187 days.

(21) Appl. No.: 13/250,270

(22) Filed: Sep. 30, 2011

(65) Prior Publication Data
US 2013/0086145 A1 Apr. 4, 2013

(51) Int. Cl.
*G06F 15/173* (2006.01)
*H04L 29/08* (2006.01)
*H04L 12/24* (2006.01)
*G06F 19/00* (2011.01)

(52) U.S. Cl.
CPC .......... *H04L 67/12* (2013.01); *H04L 41/00* (2013.01); *G06F 19/3418* (2013.01)
USPC ........................................... 709/223

(58) Field of Classification Search
CPC ....................................... H04L 41/00
USPC ............ 709/223; 707/705, 758, 781, 999.01
See application file for complete search history.

(56) References Cited

U.S. PATENT DOCUMENTS

| | | | |
|---|---|---|---|
| 5,659,694 A * | 8/1997 | Bibayan ........................ 715/788 |
| 6,332,163 B1 * | 12/2001 | Bowman-Amuah .......... 709/231 |
| 6,385,642 B1 | 5/2002 | Chlan et al. |
| 6,418,471 B1 | 7/2002 | Shelton et al. |
| 6,993,556 B1 * | 1/2006 | Seliger et al. ................. 709/203 |
| 7,346,648 B1 | 3/2008 | Seliger |
| 7,577,743 B2 * | 8/2009 | Fusari ........................... 709/227 |
| 7,647,328 B2 | 1/2010 | Fusari et al. |
| 7,660,845 B2 * | 2/2010 | Fusari ........................... 709/203 |
| 7,761,591 B2 | 7/2010 | Graham |
| 8,099,296 B2 * | 1/2012 | Mahesh et al. .................... 705/2 |
| 8,190,704 B2 | 5/2012 | Fenizia et al. |
| 8,521,860 B2 | 8/2013 | Prahalad et al. |
| 2006/0111936 A1 | 5/2006 | Mahesh et al. |
| 2007/0214238 A1 * | 9/2007 | Coppens et al. .............. 709/217 |
| 2007/0288247 A1 | 12/2007 | Mackay |
| 2008/0019500 A1 | 1/2008 | Torres et al. |
| 2008/0172457 A1 | 7/2008 | Chen et al. |
| 2008/0270177 A1 * | 10/2008 | Chamberlain ..................... 705/2 |

(Continued)

OTHER PUBLICATIONS

United States Patent and Trademark Office, Non-Final Office Action issued in connection with U.S. Appl. No. 13/250,292 on Jul. 24, 2013 (8 pages).

(Continued)

*Primary Examiner* — Lance L Barry
(74) *Attorney, Agent, or Firm* — Hanley, Flight & Zimmerman, LLC (57) ABSTRACT

Methods and apparatus for client-side context managers are disclosed. An example apparatus for use in a healthcare information system includes a primary application implemented on a client device in communication with a server; a secondary application implemented on the client device, wherein the primary application is to be initiated before the secondary application can be initiated; and a context manager integrated into the primary application to execute in connection with the primary application.

19 Claims, 7 Drawing Sheets

(56) References Cited

U.S. PATENT DOCUMENTS

| | | |
|---|---|---|
| 2009/0327310 A1 | 12/2009 | Bengtsson et al. |
| 2010/0131293 A1* | 5/2010 | Linthicum et al. ............... 705/3 |
| 2010/0131874 A1 | 5/2010 | Linthicum et al. |
| 2012/0150560 A1 | 6/2012 | Ferguson |
| 2012/0330915 A1 | 12/2012 | Mehra |
| 2013/0061303 A1* | 3/2013 | Hart et al. ....................... 726/6 |
| 2013/0086251 A1* | 4/2013 | Herlitz ........................... 709/224 |

OTHER PUBLICATIONS

United States Patent and Trademark Office, "Notice of Allowance," mailed on Oct. 21, 2013 in parent U.S. Appl. No. 13/250,292, filed Sep. 30, 2011 with inventor Sten Herlitz (35 pages).

\* cited by examiner

METHODS AND APPARATUS FOR IN-PROCESS CLIENT-SIDE CONTEXT MANAGERS

FIELD OF THE DISCLOSURE

The present disclosure relates generally to healthcare information systems and, more particularly, to methods and apparatus for client-side context managers.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage healthcare information such as, for example, patient medical histories, imaging data, test results, diagnosis information, management information, financial information, and/or scheduling information. The information may be centrally stored or divided at a plurality of locations. Healthcare practitioners may desire to access patient information or other information at various points in a healthcare workflow. For example, during surgery, medical personnel may access patient information, such as images of a patient's anatomy, which are stored in a medical information system. Further, healthcare practitioners may enter new information, such as medical history, diagnostic, financial, or treatment information into a healthcare information system before and/or after a completed medical procedure, analysis, and/or appointment. Healthcare practitioners often utilize a plurality of applications on a computing platform (e.g., a workstation) to interact with a plurality of information sources across the healthcare information system.

SUMMARY

An example apparatus for use in a healthcare information system includes a primary application implemented on a client device in communication with a server; a secondary application implemented on the client device, wherein the primary application is to be initiated before the secondary application can be initiated; and a context manager integrated into the primary application to execute in connection with the primary application.

An example method for use in a healthcare information system includes implementing a primary application on a client device in communication with a server; implementing a secondary application on the client device, wherein the primary application is to be initiated before the secondary application can be initiated; and in response to an initiation of the primary application, executing a context manager as part of the primary application.

An example tangible machine readable medium has instructions stored thereon that, when executed, cause a machine to at least implement a primary application on a client device in communication with a server; implement a secondary application on the client device, wherein the primary application is to be initiated before the secondary application can be initiated; and in response to an initiation of the primary application, execute a context manager as part of the primary application.

The foregoing summary, as well as the following detailed description of certain implementations of the methods, apparatus, systems, and/or articles of manufacture described herein, will be better understood when read in conjunction with the appended drawings. It should be understood, however, that the methods, apparatus, systems, and/or articles of manufacture described herein are not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Healthcare information systems sometimes employ a context management system, such as a Clinical Context Object Workgroup (CCOW) system. While the following description includes examples utilizing CCOW data, the example methods, apparatus, systems, and/or articles of manufacture disclosed herein can be implemented in connection with any suitable type of context data (e.g., in combination with CCOW data and/or in isolation). Typically, context data is maintained by healthcare information systems to enable synchronization across disparate applications or programs executed on a healthcare information device (e.g., a medical workstation at a hospital or clinic) being used by a healthcare practitioner (e.g., a physician, a physician's assistant, a nurse, a support staff member, administrative personnel, a member of a billing department, etc.). The CCOW standard, for example, uses a technique referred to as "context management" to provide a unified view of information associated with separate and/or different healthcare applications related to a subject (e.g., a patient, a user, a practitioner, and/or a healthcare event (e.g., an appointment, test, analysis, trauma, procedure, etc.), a location, etc.). In such instances, when a practitioner enters subject identifying data (e.g., a patient identifier or a user identifier) into a first application (e.g., an admissions program) of a CCOW-enabled system to cause a presentation of information related to the patient in the first application, a second application (e.g., a financial program) of the CCOW-enabled system automatically retrieves its respective information related to the patient and displays the same to the user of the system. That is, context management systems enable efficient cross-application workflows by automatically synchronizing common context subjects (e.g., Patient or User). As a result, the user is spared the trouble of having to log in multiple times and to look up the same subject (e.g., patient) in each application. Further, such a system aides the user in avoiding mistakes arising from the first application displaying information related to a first patient and the second application displaying information related to a second patient on the same screen. In such instances, the user may erroneously reference data related to the first patient in the first application while dealing with the second patient and, therefore, enter or provide the wrong information to a system or person. In other words, the unified view provided by a CCOW-enabled system ensures that a user interacting with multiple applications on a device is presented with the proper information across each of the applications or programs running on the device.

Figure 1:
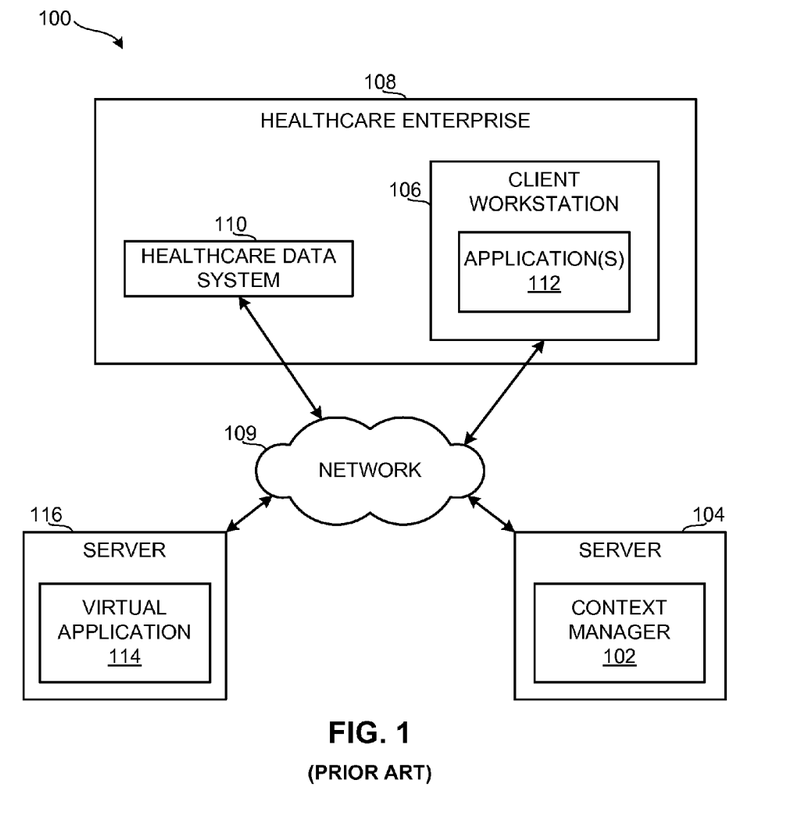
FIG. 1 is a block diagram of a prior art healthcare information system utilizing a context manager.

To implement context management, some CCOW-enabled systems utilize a central server to implement a context manager that is accessible by, for example, a healthcare workstation. In such configurations, the healthcare workstation can be referred to as a client machine in relation to the server (e.g., a remotely located server) that implements the context manager. FIG. 1 is a block diagram of an example healthcare information system 100 in which a context manager 102 is implemented on a server 104 remotely located from a client machine or workstation 106 of a healthcare enterprise 108. The context manager 102 can communicate with the client workstation 106 via a network 109. The healthcare enterprise 108 may be any type of healthcare facility such as, for example, a clinic, a physician's office, a laboratory, a testing center, etc. The example healthcare information system 100 of FIG. 1 may include additional or alternative healthcare enterprises that are configured to share healthcare information. For example, the example healthcare information system 100 of FIG. 1 may implement an XDS (Cross Enterprise Document Sharing) integration profile to facilitate the sharing (e.g., registration, distribution, access, etc.) of healthcare data among the healthcare enterprises (which are collectively referred to as an Affinity Domain in IHE (Integrating the Healthcare Enterprise) XDS terminology).

In the illustrated example of FIG. 1, the enterprise 108 includes a healthcare data system 110 in communication with the client workstation 106. Generally, the healthcare data system 110 of FIG. 1 includes one or more information systems and/or components configured to store, manipulate, analyze, and/or otherwise process healthcare information. An example healthcare data system is described in detail below in connection with FIG. 2.

The client workstation 106 includes one or more applications 112 that provide users access to the information associated with the healthcare data system 110 and/or other sources of data. Although the application(s) 112 are executed on the client workstation 106, the client workstation 106 may also utilize one or more virtual applications implemented on a server located remotely from the client workstation 106. In the illustrated example of FIG. 1, the client workstation 106 utilizes a virtual application 114 implemented on a server 116 (e.g., a Citrix server). The client workstation 106 can communicate with the virtual application 114 and/or the server 116 via the network 109. Although shown outside of the healthcare enterprise 108 in FIG. 1, in some examples the server 116 and, thus, the virtual application 114 may be considered part of the healthcare enterprise 108. For example, the server 116 and the virtual application 114 may be on a local network (e.g., the network 109) of the healthcare enterprise 108. The virtual application 114 provides a particular functionality to the client workstation 106 without the client workstation 106 having to execute (e.g., process) the virtual application 114. That is, the remotely located server 116 provides additional processing capabilities to the client workstation 106 by processing the virtual application 112 on the server 116 and providing the results of the virtual application 112 to the client workstation 106. Thus, the client workstation 106 employs a mixture of applications ranging from the application(s) 112 executing on the client workstation 106 to the virtual application 114 (and any other additional virtual applications) executing on the server 116.

In prior art systems such as the system 100 of FIG. 1 in which the context manager 102 is implemented on the server-side, certain aspects of firewall protection implemented on the client workstation 106 and/or issues with Network Address Translation (NAT) between the client workstation 106 and the remotely located servers 104 and/or 116 can prevent and/or complicate the ability of the context manager 102 to send messages to the local applications. That is, the context manager 102 and the local applications communicate using application-to-manager messages and manager-to-application messages according to, for example, the Hyper-Text Transfer Protocol (HTTP). When remotely located from the client workstation 106, the context manager 102 is restricted, at minimum, from sending manager-to-application messages to the local application(s) 112 due to firewalls and/or NAT issues implemented on the client workstation 106. Additional drawbacks of having the context manager 102 implemented on the server-side (e.g., on the server 104) include the need for additional servers, the context manager 102 and the application(s) the context manager 102 supports are subject to a single point of failure configuration, a bottleneck may form at the server 104, a load balancer may need to be employed for reliability and/or scalability, the application(s) 112 are required to make network calls to the context manager 102, etc.

As a result, some systems implement the context manager on the client-side. Although implementing the context manager on the client-side alleviates the firewall and/or NAT issues between the context manager and the local applications 112, the client-side implementation of the context manager creates and/or involves problems for the virtual application 114. In particular, the virtual application 114 is subject to firewall and/or NAT issues when communicating with a client-side context manager. For example, initiations of message exchanges between the virtual application 114 and a client-side context manager in previous systems were inhibited by firewall protections and/or NAT issues at the client device. Thus, in previous systems, the implementation of a client-side context manager hindered the availability of remotely implemented virtual applications (e.g., the virtual application 114 of FIG. 1).

Example methods, apparatus, and/or articles of manufacture disclosed herein enable utilization of virtual applications implemented on a server by a system in which a context manager is implemented on a client device of a healthcare enterprise. That is, example methods, apparatus, and/or articles of manufacture disclosed herein allow users of a client device or workstation at a healthcare enterprise to deploy a context manager on the client-side while still supporting virtual applications, thereby avoiding the costs and hindrances of a server-side implementation of the context manager. Example methods, apparatus, and/or articles of manufacture disclosed herein also improve performance of local application of the client device by eliminating the need for the local applications to make network calls to a remote server implementing the context manager. Additional aspects and advantages of the example methods, apparatus, and/or articles of manufacture disclosed herein are described below.

Figure 2:
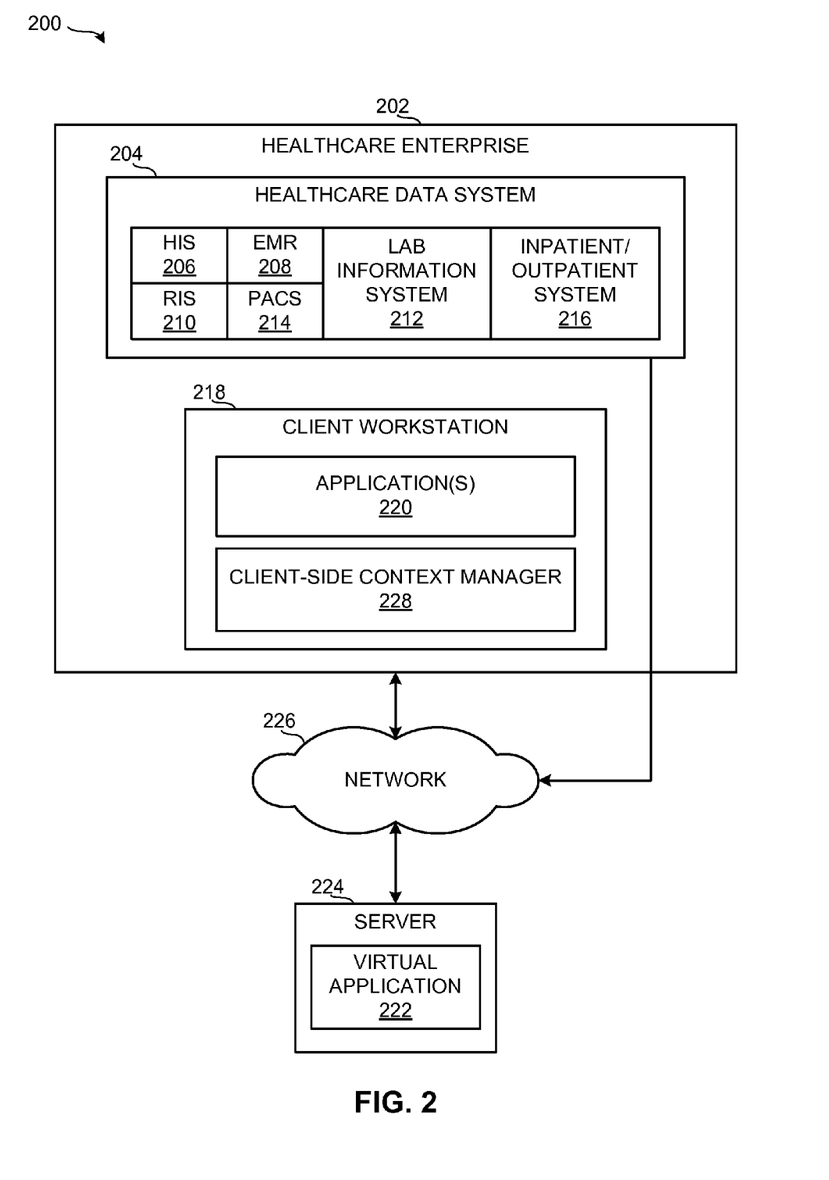
FIG. 2 is a block diagram of a healthcare information system utilizing a client-side context manager in accordance with the example methods, apparatus, and/or articles of manufacture disclosed herein.

FIG. 2 is a block diagram of a healthcare information system 200 in which the example methods, apparatus, and/or articles of manufacture disclosed herein enable a client-side implementation of a context manager. The example healthcare information system 200 of FIG. 2 includes a healthcare enterprise 202. In the illustrated example of FIG. 2, the healthcare enterprise 202 is a hospital. However, the healthcare enterprise 202 may be any type of healthcare facility or group of facilities such as, for example, a clinic, a physician's office, a laboratory, a testing center, etc. The example healthcare enterprise 202 of FIG. 2 employs a healthcare data system 204 that includes a hospital information system (HIS) 206, an electronic medical record (EMR) system 208, a radiology information system (RIS) 210, a lab information system 212, a picture archiving and communication system (PACS) 214, and an inpatient/outpatient system 216. In the illustrated example, the HIS 206, the EMR system 208, the RIS 210, the lab information system 212, the PACS 214, and the inpatient/outpatient system 216 are housed in the hospital 202 and locally archived. However, in other implementations, the HIS 206, the EMR system 208, the RIS 210, the lab information system 212, the PACS 214, and the inpatient/outpatient system 216 may be housed one or more other suitable locations. Furthermore, one or more components of the healthcare data system 204 may be combined and/or implemented together. For example, the RIS 210 and/or the PACS 214 may be integrated with the HIS 206; the PACS 214 may be integrated with the RIS 210; and/or each of the example information components 206-216 may be integrated together. Preferably, information (e.g., test results, observations, diagnosis, discharges, admissions, etc.) is entered into the information component(s) 206-216 by healthcare practitioners (e.g., radiologists, physicians, technicians, administrators, etc.) before, after, and/or during a patient examination and/or testing session. The HIS 206, the EMR system 208, the RIS 210, the lab information system 212, the PACS 214, and the inpatient/outpatient system 216 may be in communication via, for example, a Wide Area Network (WAN) such as a private network or the Internet. More generally, any of the coupling(s) described herein may be via a network. In such instances, the network may be implemented by, for example, the Internet, an intranet, a virtual private network, a wired or wireless Local Area Network, and/or a wired or wireless Wide Area Network. In some examples, the healthcare data system 204 also includes a broker (e.g., a Mitra Imaging's PACS Broker) to allow medical information and medical images to be transmitted together and stored together.

The example healthcare enterprise 202 also includes a client workstation 218. The client workstation 218 may be any equipment (e.g., a personal computer) capable of executing software that permits electronic data (e.g., medical reports) and/or electronic medical images (e.g., x-rays, ultrasounds, MRI scans, medical reports, test results, etc.) to be acquired, stored, or transmitted for viewing and operation. The workstation 218 receives commands and/or other input from a user (e.g., a physician, surgeon, nurse, or any other healthcare practitioner) via, for example, a keyboard, mouse, track ball, microphone, etc. The example workstation 218 include one or more application(s) 220 that facilitate interactions and exchanges with, for example, the healthcare data system 204 and/or any other suitable source of data and/or processing capabilities. In addition to the application(s) 220 local to the client workstation 218, the client workstation 218 utilizes a virtual application 222 implemented on a server 224 located remotely from the workstation 218. In the illustrated example of FIG. 2, the server 224 is a Citrix server through which the client workstation 218 can utilize the virtual application 222 executing on the server 224. The example client workstation 218 may access the virtual application 222 via a network 226, such as a LAN and/or the Internet. In some examples, the client workstation 218 can access the Citrix server using an alternative network (e.g., without traversing the network 226).

The example client workstation 218 also includes a client-side context manager 228. In contrast to the prior art system 100 of FIG. 1, in which the context manager 102 is implemented on the server 104, the client workstation 218 of FIG. 2 and the application(s) 220 thereof are not required to make network calls to the client-side context manager 228. As described in detail below in connection with FIG. 3, the example client-side context manager 228 maintains and enhances the ability of the client workstation 218 to utilize the virtual application 222 in comparison with previous systems. In previous systems, for virtual applications to communicate with a client-side context manager, client firewalls required opening and network(s) needed additional configuration so that the client-side devices were addressable from the virtual application server, which is especially difficult when the virtual application server is on the Internet and the client devices are on a LAN. In contrast, the example client-side context manager 228 of FIG. 2 disclosed herein is capable of establishing a connection with the virtual application 222 in spite of any firewall protection and/or NAT issues that previously restricted and/or inhibited establishment of such a connection.

Figure 3:
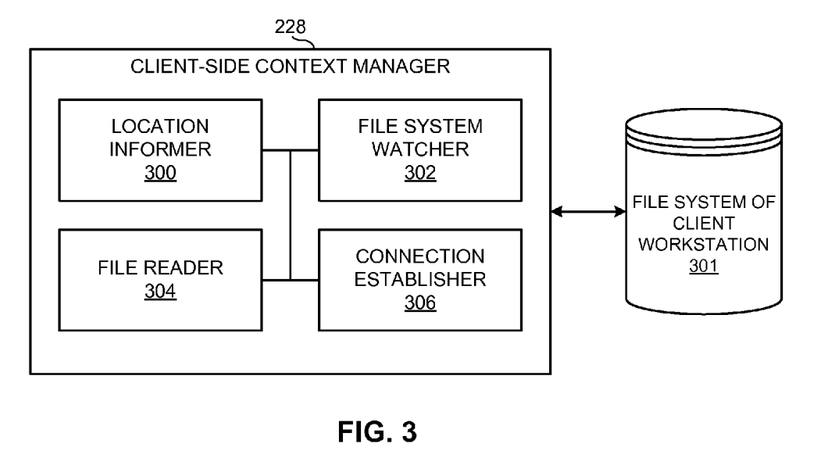
FIG. 3 is a block diagram of an example apparatus that may be used to implement the example client-side context manager of FIG. 2.

FIG. 3 is a block diagram of an example apparatus that may be used to implement the example client-side context manager 228 of FIG. 2. In the illustrated example of FIG. 3, the example client-side context manager 228 includes a location informer 300, a file system watcher 302, a file reader 304, and a connection establisher 306. While an example manner of implementing the client-side context manager 228 has been illustrated in FIG. 3, one or more of the elements, processes and/or devices illustrated in FIG. 3 may be combined, divided, re-arranged, omitted, eliminated and/or implemented in any other way. Further, the example location informer 300, the example file system watcher 302, the example file reader 304, the example connection establisher 306, and/or, more generally, the example client-side context manager 228 of FIG. 3 may be implemented by hardware, software, firmware and/or any combination of hardware, software and/or firmware. Thus, for example, any of the example location informer 300, the example file system watcher 302, the example file reader 304, the example connection establisher 306, and/or, more generally, the example client-side context manager 228 of FIG. 3 could be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended apparatus or system claims are read to cover a purely software and/or firmware implementation, at least one of the example location informer 300, the example file system watcher 302, the example file reader 304, the example connection establisher 306, and/or, more generally, the example client-side context manager 228 of FIG. 3 are hereby expressly defined to include a tangible and/or non-transitory computer readable medium such as a physical memory, DVD, CD, etc. storing the software and/or firmware. Further still, the example client-side context manager 228 of FIG. 3 may include one or more elements, processes and/or devices in addition to, or instead of, those illustrated in FIG. 3, and/or may include more than one of any or all of the illustrated elements, processes and devices.

The example client-side context manager 228 of FIG. 3 enables a connection between the virtual application 222 and the client-side context manager 228 such that the context manager 228 can be implemented on the client workstation 218 that utilizes the virtual application 222. That is, the example client-side context manager 228 of FIG. 3 enables the client workstation 218 to have the context manager 228 implemented locally and, at the same time, to readily utilize virtual applications implemented on a remotely located server (e.g., the server 224 of FIG. 2). As described above, virtual applications at remote servers of previous systems are sometimes prevented from initiating a connection with a context manager implemented on a client machine due to, for example, firewall protection and NAT issues. However, the example client-side context manager 228 of FIG. 3 enables the virtual application 222 to initiate such a connection by providing access to a dedicated location of a file system of the client machine and monitoring that location for an item placed there by the virtual application 222.

In particular, the example location informer 300 of FIG. 3 provides the virtual application 222 with access to a location (e.g., a folder) in a file system 301 of the client workstation 218 of FIG. 2. The location or folder is selected and dedicated (e.g., by the context manager 228) to the virtual application 222 and/or other virtual applications. Additional locations or folders are dedicated to other virtual applications, if any, utilized by the client workstation 218. In other words, for each virtual application utilized by the client workstation 218, a location in the file system 301 is selected for the respective virtual application. Alternatively, a single location (e.g., folder) can be dedicated to multiple virtual applications. In such instances, different file names can be used to write different files, each corresponding to a virtual application, into the single file.

Some services (e.g., Citrix, Microsoft® RDS) provide a mechanism that allows the virtual application 222 access to the dedicated folder on the client workstation 218. Such a mechanism involves mapping a drive letter to the dedicated folder and exposing that drive to the virtual application 222. The virtual application 222 can then access the drive using an indicator (e.g., as \\tsclient\Z), which could be a configurable setting that a SDK (Software Development KIT) component or COM component would read from a file.

Thus, in some examples, the location informer 300 utilizes an SDK component or a plug-in model configured to inform the virtual application 222 of how to communicate with the dedicated location. In many instances, CCOW-enabled applications use a third party SDK component to handle all messaging. In the illustrated example of FIG. 3, the SDK can be customized, transparently to the user, to include the protocol disclosed herein for finding and utilizing a file location at the client workstation 218. Additionally or alternatively, the location informer 300 can provide a CCOW reference to the context manager 228 to CCOW-enabled applications (e.g., the virtual application 222) that can be used to find the context manager 228. According to the CCOW specification, the CCOW reference can be in the form of a COM (Component Object Model) object or a HTTP URL (Hyper-Text Transfer Protocol universal resource locator). In the illustrated example of FIG. 3, the location informer 300 provides the COM object to the server 224 that would encapsulate and mediate access to the dedicated folder. To enable the virtual application 222 to utilize the dedicated location of the file system 301, the COM object exposes the virtual application 222 to an application programming interface (API) (e.g., a standard CCOW API). That is, the COM object mediates access to the dedicated location for the virtual application 222. The COM object can run in-process with the virtual application 222. The COM object provided by the location informer 300 also enables the virtual application 222 to write an item (e.g., file) to the location. Further, the exposure to the API provided to the virtual application by the COM object also enables the virtual application 222 to, when a connection is desired between the server 224 and the client workstation 218 (e.g., so that the client workstation 218 can utilize the virtual application 222), write an item to the dedicated location in the file system 301. As described above, the virtual application 222 is restricted from sending a conventional connection request to the client-side context manager 228 due to, for example, firewall protections and/or NAT issues. Thus, the example client-side context manager 228 of FIG. 3 provides an alternate method and/or mechanism for the virtual application to initiate a connection with the context manager 228 and the application(s) 220 of the client workstation 218. The item or file that the virtual application 222 is to write to the location includes instructions for the client-side context manager 228 to establish a connection with the virtual application 222. For example, the item written to the dedicated location may include an address (e.g., an HTTP URL) to which the client-side context manager 228 can send a message to request the connection.

The example file system watcher 302 monitors the dedicated location of the file system 301 (along with other dedicated locations of the file system corresponding to other virtual application(s)) corresponding to the virtual application 222 to detect a write of the item by the virtual application 222. The example file system watcher 302 detecting the item being written in the dedicated location of the file system 301 triggers the client-side context manager 228 to establish a connection with the virtual application 222. To establish the connection, the example file reader 304 analyzes the item written into the dedicated location to identify the instructions for connecting to the virtual application 222. As described above, the virtual application 222 includes instructions, such as an address associated with the server 224, in the item to enable the client-side context manager 228 to communicate with the virtual application 222.

The example file reader 304 of FIG. 3 conveys the results of the analysis to the connection establisher 306. The example connection establisher 306 uses the information conveyed thereto from the file reader 304 to generate and transmit a message to the virtual application 222 at the server 224. The message generated and transmitted by the connection establisher 306 is a request that the virtual application 222 can accept by replying to the message. The virtual application 222 initiates a listener (e.g., in conjunction with placing the item in the dedicated location in the file system 301) that is capable of receiving the request from the client workstation 218. A reply from the virtual application 222 to the request establishes a connection (e.g., a bi-directional socket connection or a one-way socket connection, such as HTTP) between the client-side context manager 228 and the virtual application 222. As result, the virtual application 222 and the client-side context manager 228 can convey message to each other in both directions (e.g., from the virtual application 222 to the context manager 228 and from the context manager 228 to the virtual application 222) without firewall protections and/or NAT issues interfering with such an exchange. As described above, firewall protection and NAT issues caused virtual applications at remote servers difficulties when initiating a connection with a context manager implemented on a client machine. However, the example client-side context manager 228 of FIG. 3 enables the virtual application 222 to indirectly initiate such a connection by enabling a write to the dedicated location of the file system 301 and monitoring that location for an item placed there by the virtual application 222. The item being placed in the location by the virtual application 222 causes the client-side context manager 228 to directly initiate the connection with the virtual application 222 by sending a connection request via the connection establisher 306. The direct initiation by the client-side context manager 228 is not blocked by the firewall protection and avoids the NAT issues that prevent a direct initiation by the virtual application 222.

In some examples, the connection establisher 306 provides an alternative manner to avoid firewall and/or NAT issues that prevent the virtual application 222 from communicating with a context manager implemented on the client side. In particular, the connection establisher 306 can establish a two-way socket connection to a server-side intermediary component upon startup. The server-side intermediary component may be provided to the server 224 by, for example, the connection establisher 306. A locator server on the server 224 would provide a URL-reference to the intermediary component, thereby making the intermediary component appear to be a server-side context manager to the virtual application 222. However, in actuality, the intermediary component would forward all traffic to the client-side context manager via the pre-established socket connection. This configuration also avoids the firewall and NAT issues described above.

Figure 4:
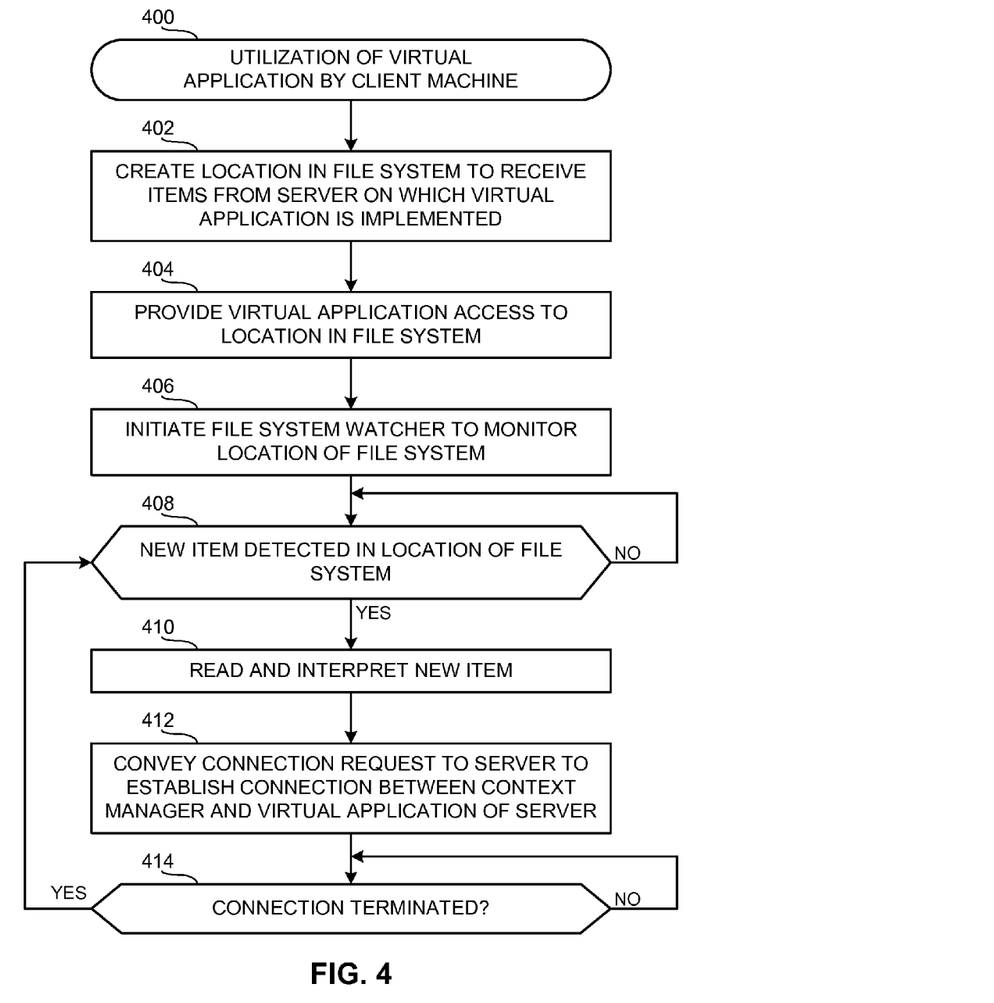
FIG. 4 is a flow diagram representative of example machine readable instructions that may be executed to implement the example client-side context manager of FIGS. 2 and/or 3.

FIG. 4 is a flow diagram representative of example machine readable instructions that may be executed to implement the example client-side context manager of FIGS. 2 and/or 3. In the example of FIG. 4, the machine readable instructions comprise programs and/or routines for execution by a processor such as the processor 712 shown in the example processor platform 710 discussed below in connection with FIG. 7. The programs may be embodied in software stored on a computer readable medium such as a CD-ROM, a floppy disk, a hard drive, a digital versatile disk (DVD), and/or any form of physical memory associated with the processor 712, but the entire program and/or parts thereof could alternatively be executed by a device other than the processor 712 and/or embodied in firmware or dedicated hardware. Further, although the example programs are described with reference to the flowcharts illustrated in FIG. 4, many other methods of implementing the example client-side context manager 228 may alternatively be used. For example, the order of execution of the blocks may be changed, and/or some of the blocks described may be changed, eliminated, or combined.

As mentioned above, the example processes of FIG. 4 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example processes of FIG. 4 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

FIG. 4 begins with recognition that the client workstation 218 utilizes the virtual application 222 (block 400). A location in the file system 301 of the client workstation 218 is selected and/or dedicated to receive items from the server 224 (block 402). Further, the location informer 300 provides the virtual application 222 with access to the newly created and/or designated location in the file system 301 (block 404). In some examples, the location informer 300 provides the access via a COM object that enables the virtual application 222 to access the location of the file system 301 and the protocol by which an item may be placed at the location of the file system 301. The client-side context manager 228 then initiates the file system watcher 302 to monitor the location of the file system 301 (block 406). When the file system watcher detects a new item (e.g., file) in at the designated location (block 408), the file reader 304 analyzes the new item (block 410). The file reader 304 identifies instructions including, for example, an address at which the virtual application 222 can be reached, for communicating a message to the virtual application 222 (e.g., via the server 224). Using the information garnered from the new item by the file reader 304, the connection establisher 306 conveys a connection request to the server 224 to begin the establishment of the connection between the client-side context manager 228 and the virtual application 222 (block 412). Thus, while the client-side context manager 228 technically initiates the connection, the establishment of the connection was triggered by the virtual application 222 when the virtual application 222 placed the new item in the monitored location of the file system 310. If the established connection between the client-side context manager 228 and the virtual application 222 is terminated (block 414), control passes to block 408 and the file system watcher 302 continues monitored the dedicated location for new items from the virtual application 222.

Figure 5:
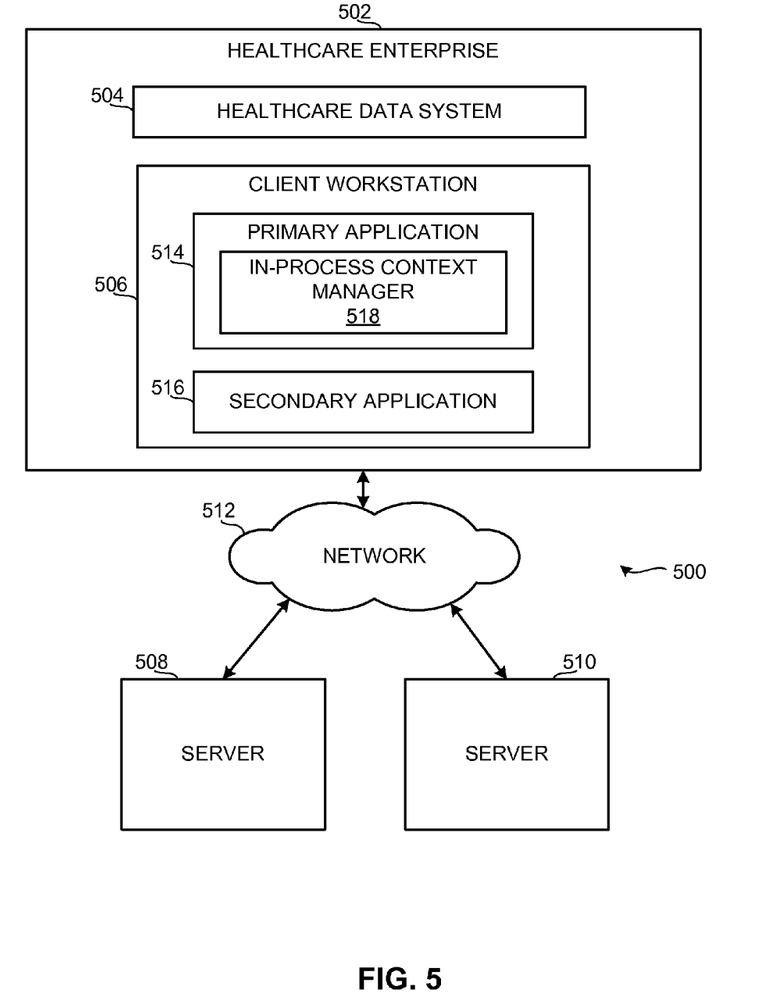
FIG. 5 is a block diagram of a healthcare information system utilizing an in-process context manager in accordance with the example methods, apparatus, and/or articles of manufacture disclosed herein.

FIG. 5 is a block diagram of a healthcare information system 500 in which the example methods, apparatus, and/or articles of manufacture disclosed herein to enable an in-process context manager on a client machine can be implemented. The example healthcare information system 500 of FIG. 5 includes a healthcare enterprise 502. Similar to the healthcare enterprise 202 of FIG. 2, the example healthcare enterprise 500 is a hospital and employs a healthcare data system 504. However, the healthcare enterprise 502 may be any type of healthcare facility or group of facilities such as, for example, a clinic, a physician's office, a laboratory, a testing center, etc. The example healthcare data system 504 of FIG. 5 may be similar to the healthcare data system 202 of FIG. 2. Further, the example healthcare enterprise 502 of FIG.

5 includes a client workstation 506 that interacts with, for example, the healthcare data system 504. The healthcare data system 504 and the client workstation 506 are in communication with any suitable external machine(s) and/or system(s), such as first and second servers 508 and 510 via a network 512 and/or directly. The first and/or second server 508, 510 may include, for example, virtual application(s) utilized by the client workstation 506.

The example client workstation 506 of FIG. 5 includes a primary application 514 and a secondary application 516. The primary application 514 and the secondary application 516 enable a healthcare practitioner using the client workstation 506 to interact with, for example, the healthcare data system 504 and/or the servers 508 and 510. For example, the primary application 514 and/or the secondary application 516 may retrieve information from a corresponding component of the healthcare data system 504, configure equipment associated with a corresponding component of the healthcare data system 504, present data associated with a corresponding component of the healthcare data system 504, and/or otherwise interact with one or more components of the healthcare data system 504.

In the illustrated example of FIG. 1, the primary application 514 implements a program that the user of the client workstation 506 typically and/or is required to open first at the onset of a session with the client workstation 506. For example, the primary application 514 may implement an authentication program to verify the identity of users attempting to logon to the client workstation 506. In some examples, before the secondary application 516 can be launched, the authentication program of the primary application 514 is required to verify the identity of a user of the client workstation 506. Additionally or alternatively, the primary application 514 may provide an overview of a workflow associated with the user (e.g., who may be identified via login information) and can be used to manage the workflow and the tasks thereof. Additionally or alternatively, the primary application 514 may implement a launch bar that the user would have running on a desktop including icons that launch healthcare applications (e.g., the secondary application 516). The secondary application 516 is more specific relative to the primary application 514 in that the secondary application 516 is dedicated to particular component(s) of the healthcare data system 504. For example, the secondary application 516 may implement an interface program that facilitates interactions with a PACS or an EMR.

The example client workstation 506 also includes an example in-process context manager 518 configured in accordance with the example methods, apparatus, and/or articles of manufacture disclosed herein. In previous systems, a client-side context manager is executed as a separate process as the applications that utilize the context manager. In contrast to previous systems, the in-process context manager 518 disclosed herein is executed inside the process of the primary application 514. That is, instead of providing the context manager to the client workstation 506 and having the client workstation 506 run the context manager as a standalone program (as in previous systems), the example in-process context manager 518 of FIG. 5 is integrated into the primary application 514. Thus, as the example in-process context manager 518 is integrated with the primary application 514, the example in-process context manager can be executed in response to an initiation of the primary application 514.

In some examples, the in-process context manager 518 can be enabled to be implemented as a client-side mechanism by the example methods, apparatus, and/or articles of manufacture disclosed above in connection with FIGS. 2-4. That is, the example in-process context manager 518 of FIG. 5 can, in addition to the functionality described below, establish a connection with a virtual application implemented on a server in response to the virtual application placing an item in a monitored file system location on the client workstation 506. In other words, the example client-side context manager 228 of FIGS. 2 and/or 3 can be integrated into a primary application on the client workstation 218 of FIG. 2 as described in connection with FIGS. 5 and 6 below.

In some examples, the in-process context manager 518 is integrated into the primary application 514 by placing the content (e.g., logic and/or instructions) of the context manager 518 inside a dynamically linked library (DLL) and providing the DLL as an optional component in a SDK that the client workstation applications 514 and 516 use to communicate with a context manager (e.g., a CCOW context manager). In such instances, the primary application 514 can reference the DLL including the context manager 518 to execute the context manager 518 as part of the primary application 514. As a result, when a user of the client workstation 514 initiates a session and opens the primary application 514, which, in some instances, is necessary before proceeding to use other aspects of the client workstation 506 (e.g., the secondary application 516), the in-process context manager 518 is automatically initiated and begins running.

In some examples, executing the context manager 518 as part of the primary application 514 includes executing a first thread associated with the context manager 518 in parallel with a second thread associated with one or more aspects of the primary application 514. Of course, execution of the context manager 518 and/or the primary application 514 may involve a more than one thread each, as many threads can be executed in connection with the context manager 518 and/or the primary application 514.

In instances in which the primary application 514 includes an authentication program, the in-process context manager 518 can be executed in response to the initiation of the primary application 514 or in response to an identity verification (e.g., a successful login via the authentication program).

The example in-process context manager 518 of FIG. 5 and the execution thereof within the primary application 514 improves the performance of the context management by enabling a one-hop communication requirement between applications rather than a two-hop (or more) communication requirement of the prior art. Further, the in-process context manager 518 can be deployed as part of the primary application 514 instead of as a standalone program, thereby simplifying the implementation of the context management system for the client workstation 506.

Figure 6:
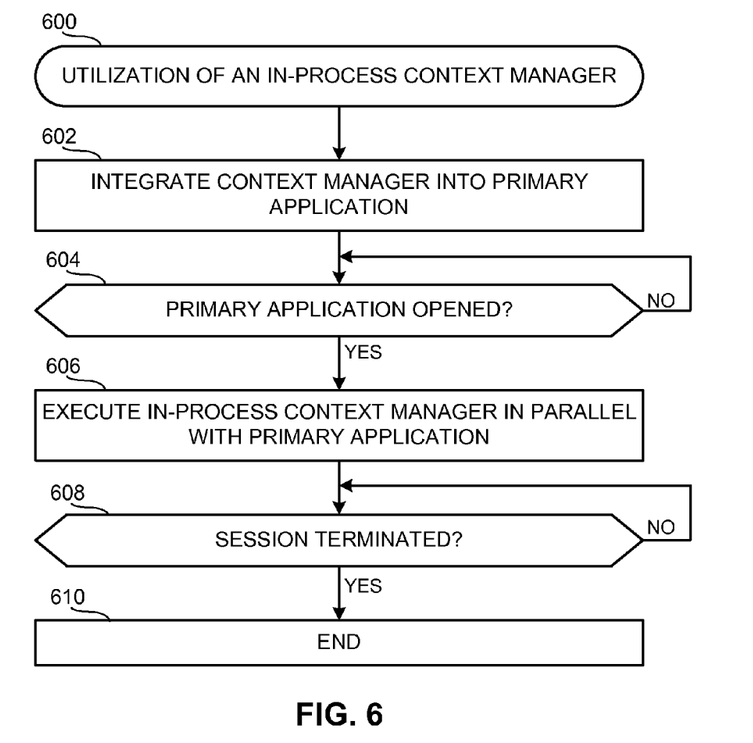
FIG. 6 is a flow diagram representative of example machine readable instructions that may be executed to implement the example in-process context manager of FIG. 5.

FIG. 6 is a flow diagram representative of example machine readable instructions that may be executed to implement the example in-process context manager of FIG. 5. In the example of FIG. 6, the machine readable instructions comprise programs and/or routines for execution by a processor such as the processor 712 shown in the example processor platform 710 discussed below in connection with FIG. 7. The programs may be embodied in software stored on a computer readable medium such as a CD-ROM, a floppy disk, a hard drive, a digital versatile disk (DVD), and/or any form of physical memory associated with the processor 712, but the entire program and/or parts thereof could alternatively be executed by a device other than the processor 712 and/or embodied in firmware or dedicated hardware. Further, although the example programs are described with reference to the flowcharts illustrated in FIG. 6, many other methods of implementing the example in-process context manager 518 may alternatively be used. For example, the order of execution of the blocks may be changed, and/or some of the blocks described may be changed, eliminated, or combined.

As mentioned above, the example processes of FIG. 6 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example processes of FIG. 6 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

FIG. 6 begins with recognition that the in-process context manager 518 is to be utilized by the client workstation 506 of FIG. 5 (block 600). The example in-process context manager 518 is integrated into the primary application 514 of FIG. 5 by, for example, placing logic associated with the in-process context manager 518 in a library (e.g., a DLL) and providing access to the DLL to the client workstation 506 (block 602). In the illustrated example, a user of the client workstation 506 is required to login using the primary application 514 before utilizing other aspects of the client workstation 506. When a user opens the primary application 514 (block 604), the in-process context manager 518 is executed in parallel with the primary application 514 (block 606). Thus, the in-process context manager 518 is not required to be a standalone program or process and, instead, is part of one of the applications implemented on the client workstation 506. The example of FIG. 6 ends at block 610 when the session is terminated at block 608. Otherwise, the in-process context manager 518 continues to execute in parallel with the primary application 514.

Figure 7:
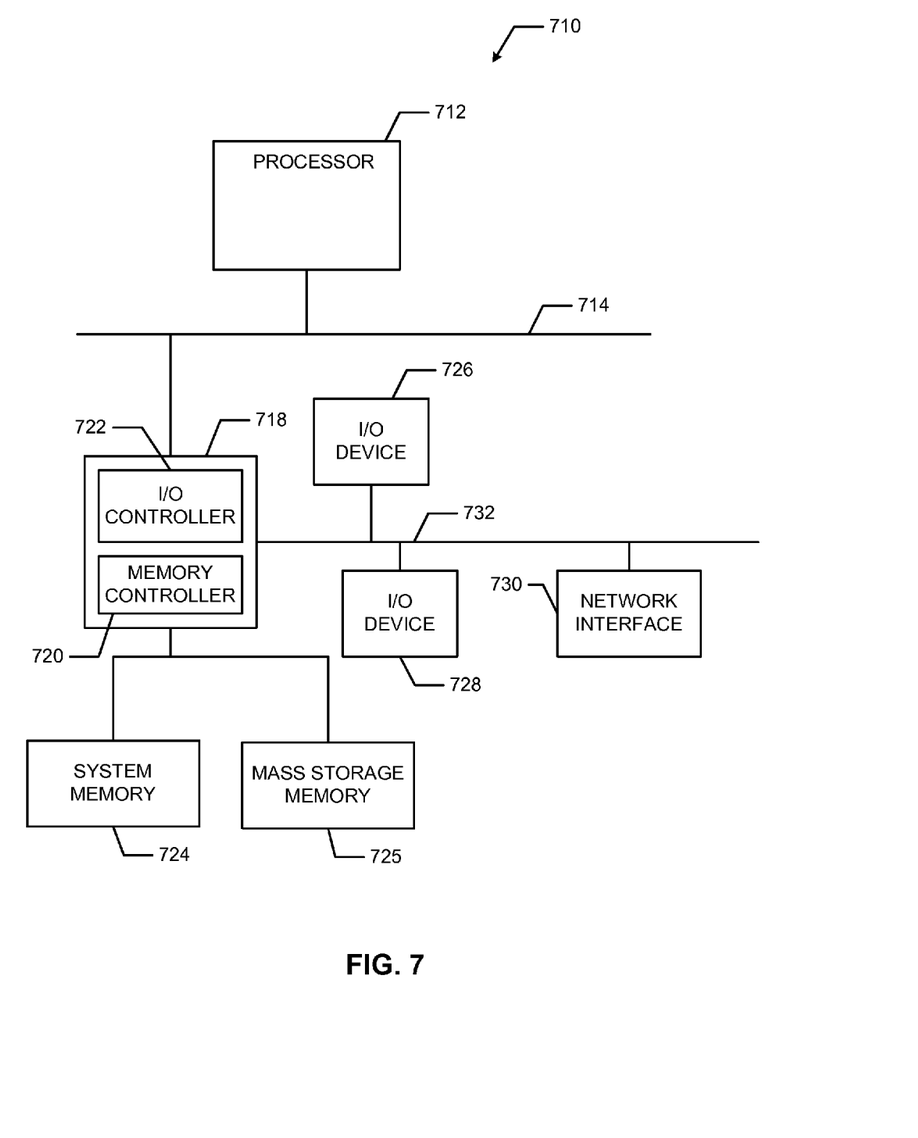
FIG. 7 is a block diagram of an example processor system that may be used to execute the machine readable instructions of FIG. 4 to implement the example client-side context manager of FIGS. 2 and/or 3 and/or the machine readable instructions of FIG. 6 to implement the example in-process context manager of FIG. 5.

FIG. 7 is a block diagram of an example processor system 710 that may be used to implement the apparatus and methods disclosed herein. As shown in FIG. 7, the processor system 710 includes a processor 712 that is coupled to an interconnection bus 714. The processor 712 may be any suitable processor, processing unit or microprocessor. Although not shown in FIG. 7, the system 710 may be a multi-processor system and, thus, may include one or more additional processors that are identical or similar to the processor 712 and that are communicatively coupled to the interconnection bus 714.

The processor 712 of FIG. 7 is coupled to a chipset 718, which includes a memory controller 720 and an input/output (I/O) controller 722. As is well known, a chipset typically provides I/O and memory management functions as well as a plurality of general purpose and/or special purpose registers, timers, etc. that are accessible or used by one or more processors coupled to the chipset 718. The memory controller 720 performs functions that enable the processor 712 (or processors if there are multiple processors) to access a system memory 724 and a mass storage memory 725.

The system memory 724 may include any desired type of volatile and/or non-volatile memory such as, for example, static random access memory (SRAM), dynamic random access memory (DRAM), flash memory, read-only memory (ROM), etc. The mass storage memory 725 may include any desired type of mass storage device including hard disk drives, optical drives, tape storage devices, etc.

The I/O controller 722 performs functions that enable the processor 712 to communicate with peripheral input/output (I/O) devices 726 and 728 and a network interface 730 via an I/O bus 732. The I/O devices 726 and 728 may be any desired type of I/O device such as, for example, a keyboard, a video display or monitor, a mouse, etc. The network interface 730 may be, for example, an Ethernet device, an asynchronous transfer mode (ATM) device, an 802.11 device, a DSL modem, a cable modem, a cellular modem, etc. that enables the processor system 710 to communicate with another processor system.

While the memory controller 720 and the I/O controller 722 are depicted in FIG. 7 as separate blocks within the chipset 718, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A healthcare information system, comprising:
a primary application of the healthcare information system implemented on a client device in communication with a server, the primary application to facilitate launching of a secondary application implemented on the client device, wherein the primary application is required to be initiated before the secondary application can be initiated; and
a context manager integrated into the primary application and to be automatically executed inside a process of the primary application in response to the primary application being initiated, the context manager to provide context information to the secondary application launched via the primary application.

2. A healthcare information system as defined in claim 1, wherein the context manager is to execute in parallel with the primary application.

3. A healthcare information system as defined in claim 1, wherein the primary application comprises an authentication program.

4. A healthcare information system as defined in claim 3, wherein the secondary application requires authentication before launching.

5. A healthcare information system as defined in claim 1, wherein the client device comprises a client workstation associated with a healthcare enterprise.

6. A method for use in a healthcare information system, comprising:
implementing a primary application of the healthcare information system on a client device in communication with a server, the primary application to facilitate launching of a secondary application;
implementing the secondary application on the client device, wherein the primary application is required to be initiated before the secondary application can be initiated; and
in response to an initiation of the primary application, executing a context manager inside a process of the primary application, wherein the context manager is integrated with the primary application, the context to provide context information to the secondary application launched via the primary application.

7. A method as defined in claim 6, wherein executing the context manager inside the process of the primary application comprises executing a first thread associated with the context manager in parallel with a second thread associated with the primary application.

8. A method as defined in claim 6, wherein executing the context manager as part of the primary application comprises the primary application referencing a Dynamically Linked Library file including content related to the context manager.

9. A method as defined in claim 6, wherein the primary application comprises an authentication program.

10. A method as defined in claim 9, wherein the secondary application requires authentication before launching.

11. A method as defined in claim 9, wherein executing the context manager in response to the initiation of the primary application comprises executing the context manager in response to the authentication program verifying an identity of a user.

12. A method as defined in claim 9, wherein executing the context manager in response to the initiation of the primary application comprises executing the context manager in response to a user opening the authentication program.

13. A tangible computer readable medium storing instructions that, when executed, cause a machine to at least:
implement a primary application on a client device of a healthcare information system, the client device in communication with a server, the primary application to facilitate launching of a secondary application;
implement the secondary application on the client device, wherein the primary application is required to be initiated before the secondary application can be initiated; and
in response to an initiation of the primary application, execute a context manager inside a process of the primary application, the context manager integrated with the primary application and to provide context information to the secondary application launched via the primary application.

14. A tangible computer readable medium as defined in claim 13, the instructions to cause the machine to execute the context manager as part of the primary application by executing a first thread associated with the context manager in parallel with a second thread associated with the primary application.

15. A tangible computer readable medium as defined in claim 13, the instructions to cause the machine to execute the context manager as part of the primary application by causing the primary application to reference a Dynamically Linked Library file including content related to the context manager.

16. A tangible computer readable medium as defined in claim 13, wherein the primary application comprises an authentication program.

17. A tangible computer readable medium as defined in claim 16, the instructions to cause the secondary application to require authentication before launching.

18. A tangible computer readable medium as defined in claim 16, the instructions to cause the machine to execute the context manager in response to the initiation of the primary application by causing the context manager to execute in response to the authentication program verifying an identity of a user.

19. A tangible computer readable medium as defined in claim 16, the instructions to cause the machine to execute the context manager in response to the initiation of the primary application by causing the context manager to execute in response to a user opening the authentication program.

* * * * *